(12) United States Patent
Berte' et al.

(10) Patent No.: US 8,864,851 B2
(45) Date of Patent: Oct. 21, 2014

(54) COMPOSITIONS OF FLUORESCENT WHITENING AGENTS

(71) Applicant: 3V Sigma S.p.A., Milan (IT)

(72) Inventors: Ferruccio Berte', Bergamo BG (IT);
Marco Brena, Bergamo BG (IT);
Massimo Fabbi, Mozzo BG (IT);
Francesco Maestri, Bergamo BG (IT)

(73) Assignee: 3V Sigma S.p.A., Milan (IT)

( * ) Notice: Subject to any disclaimer, the term of this patent is extended or adjusted under 35 U.S.C. 154(b) by 0 days.

(21) Appl. No.: 14/351,269

(22) PCT Filed: Oct. 25, 2012

(86) PCT No.: PCT/IB2012/055868
§ 371 (c)(1),
(2), (4) Date: Apr. 11, 2014

(87) PCT Pub. No.: WO2013/064946
PCT Pub. Date: May 10, 2013

(65) Prior Publication Data
US 2014/0252262 A1  Sep. 11, 2014

(30) Foreign Application Priority Data

Nov. 4, 2011 (IT) .............................. MI2011A2003

(51) Int. Cl.
*D06L 3/12* (2006.01)
*C07D 253/00* (2006.01)
*C11D 3/42* (2006.01)

(52) U.S. Cl.
CPC ................ *C11D 3/42* (2013.01); *D06L 3/1228* (2013.01)
USPC ................................... 8/648; 8/688; 544/180

(58) Field of Classification Search
USPC ........................................ 8/648, 688; 544/180
See application file for complete search history.

(56) References Cited

U.S. PATENT DOCUMENTS

| 4,468,341 A | 8/1984 | Beyer |
| 6,025,490 A | 2/2000 | Feldhues et al. |

FOREIGN PATENT DOCUMENTS

| EP | 1612209 | 1/2006 | |
| GB | 1542907 | 3/1979 | |
| WO | 2004005617 | 1/2004 | |
| WO | WO 2005/028749 A1 * | 3/2005 | ............... D06L 3/12 |
| WO | 2006061399 | 6/2006 | |

OTHER PUBLICATIONS

STIC Search Report dated Jun. 23, 2014.*
International Search Report PCT/IB2012/055868, (2012).

* cited by examiner

*Primary Examiner* — Eisa Elhilo
(74) *Attorney, Agent, or Firm* — Silvia Salvadori, P.C.

(57) ABSTRACT

The present invention relates to whitening compositions, processes for obtaining such compositions, stable aqueous solutions of such compositions and the use of such compositions for whitening of textile fibers, paper and in detergency.

19 Claims, No Drawings

COMPOSITIONS OF FLUORESCENT WHITENING AGENTS

CROSS-REFERENCE TO RELATED APPLICATIONS

This application is a 371 of PCT/IB2012/055868, filed Oct. 25, 2012, which claims the benefit of Italian Patent Application No. MI2011A002003, filed Nov. 4, 2011, the contents of each of which are incorporated herein by reference.

FIELD OF THE INVENTION

The present invention relates to whitening compositions, processes for obtaining such compositions, stable aqueous solutions of such compositions and use of such compositions for the whitening of textile fibers, paper and in detergency.

BACKGROUND OF THE INVENTION

The use of whitening agents to impart a greater degree of white in products such as paper, cardboard, fabrics and non-wovens is well known. The most widely used whitening agents in paper and cardboard industry are the derivatives of 4,4'-bis-[1,3,5-triazinyl]-diaminostilbene-2,2'-disulfonic acid substituted at the triazine ring with aniline groups and alkanolamine groups. The aniline groups may in turn contain other sulphonic groups which however, by increasing the solubility in water of the molecules, reduce their affinity towards the cellulose fibers that form the paper and tissues and lead to lower performance in terms of degree of white.

For reasons of ease of processing, the paper industry requires that these whitening agents are supplied in liquid forms of fluid aqueous dispersion or, most preferably, of an aqueous solution stable for at least several months at temperatures from 5 to 40° C.

The stilbene whitening agents that are derivatives of 4,4'-bis-[1,3,5-triazinyl]-diaminostilbene-2,2'-disulfonic acid substituted at the triazine ring with aniline groups and alkanolamine groups, preferred in this field, are not easily soluble in water, therefore the production of the related concentrated and stable aqueous solutions has required in the past the addition of significant amounts, even up to 30%, of additives such as solubilizers, for example urea, caprolactam, ethylene glycol and polyglycols.

However, the added solubilizers do not have great affinity for cellulose and do not contribute significantly to the performance of the product thus resulting, at the end of the process of paper production, in unwanted pollutants. For example, when whitening agents are used in solutions formulated with urea, a heavy pollutant load of nitrogen byproducts and ammonia is introduced in the liquid effluents of the process.

A further problem derives from the inevitable presence of inorganic chlorides in the whitening agent solutions, for example sodium chloride, which is derived from the processes of synthesis of whitening agents themselves. In fact, all industrial processes of production of triazine substituted stilbene whitening agents, require the use of cyanuric chloride as reagent, whose reaction in successive stages with different necessary amino products inevitably leads to the generation of large quantities of inorganic chlorides that are difficult to eliminate.

The inorganic chloride residues generate instability in concentrated aqueous solutions of whitening agents and therefore has been so far indispensable to significantly reduce the content thereof, by inevitably resorting to costly separation osmotic techniques, for obtaining compositions stable over time.

GB 1356016 describes a method for the optical whitening of paper through the use of substantially aqueous suspensions of a compound having the following formula:

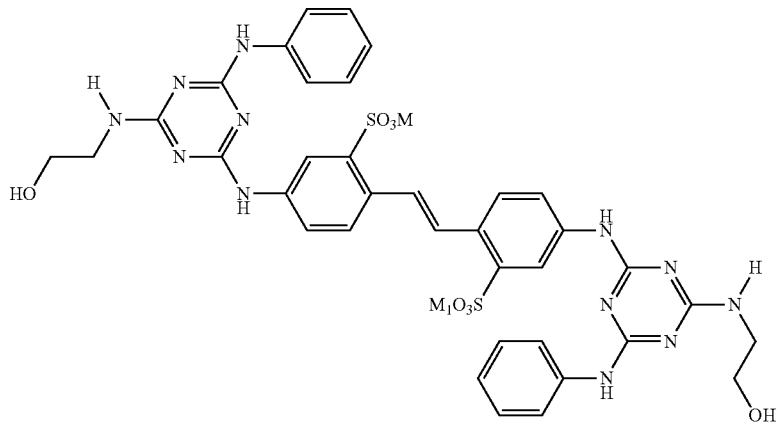

wherein M and $M_1$ represent hydrogen, an alkali metal, an alkaline earth metal or ammonium.

U.S. Pat. No. 3,012,971 describes compositions for whitening paper consisting of aqueous solutions of concentrated acid, 4,4'-bis-[2-phenylamino-4-dietanolamino-1,3,5-triazinyl]-diaminostilbene-2,2'-disulfonic acid or of a salt thereof in admixture with alkanolamines, wherein the proportion by weight of alkanolamines compared to whitening agents varies from 0.5:1 to 3.0:1. Since the molecular weight of the alkanolamines is much lower than that of the whitening agents, this interval reflects a large excess of alkanolamine compared to the whitening agent. However, such high quantities of alkanolamines, compared to the whitening power of the composition, are not acceptable from the ecological point of view.

WO 2005/028749 describes aqueous compositions comprising stilbene whitening agents and alkanolamines. This document does not describe any example of a composition comprising a tertiary alkanolamine. Furthermore, it is not mentioned the problem of the effect of the inorganic chlorides on the stability of the solution.

U.S. 2010/0159763 describes aqueous compositions of fluorescent whitening agents substituted at the triazine rings by propionamide amino groups, having the following formula:

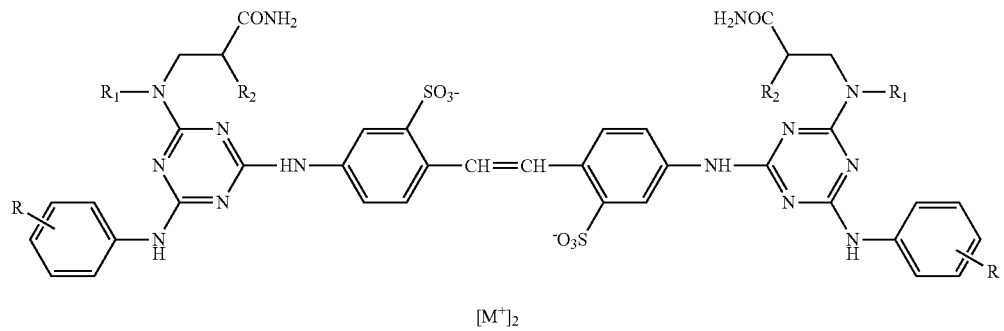

in which at least 25% of the ions [M⁺] associated with the sulfonic group have been replaced by $(CH_3)_2NH^+CH_2CH_2OH$ ions. However, in such compositions it is necessary to reduce the content of inorganic salts with suitable osmosis processes in order to guarantee the stability of the formulation.

U.S. Pat. No. 4,112,226 and GB 1286459 describe methods for the removal of triazine derivative impurities from fluorescent whitening agents. In fact these impurities, if present in a too high concentration, make the fluorescent whitening agent not suitable for use in the detergent compositions described in those publications, by causing colors and odors of the detergent compositions themselves. The methods described in these documents are based on a boiling step of the impure fluorescent whitening agents in alkaline or alcoholic aqueous solutions and subsequent filtration step of the insoluble whitening agent. However, the described methods do not allow to reduce the content of residual impurities in the agent whitening to below about 2000 ppm. Furthermore, the stability problem of the aqueous solutions of the fluorescent whitening agents is not considered nor tackled.

SUMMARY OF THE INVENTION

Object of the present invention is to provide a composition of whitening agents that can be produced by a simple and economical process comprising no purification steps, said composition nevertheless being particularly stable in aqueous solution, even in the presence of inorganic chlorides normally remaining at the end of the synthesis and without the addition of stabilizing additives or solubilizers.

Said object is achieved with a composition whose main features are specified in the first claim, a process whose main features are specified in claim 10, a product obtained through this process whose main features are specified in claim 16, an aqueous solution whose main features are specified in claim 17 and a use whose main features are specified in claims 18.

DETAILED DESCRIPTION OF THE INVENTION

It has in fact been surprisingly discovered that the compositions of certain amine salts of fluorescent whitening agents, although being particularly stable in aqueous solution, are very sensitive to the presence of low levels of triazine impurities and in particular of 2-hydroxy-4,6-dianilino-1,3,5-triazine (AAHT) that are inevitably formed during the synthesis of the optical brightener.

If this impurity exceeds a threshold of minimum concentration, much less than 2000 ppm, this results in a reduction of the stability of the composition in aqueous solution.

At very low levels of such impurity, the compositions of certain fluorescent whitening agents and of particular tertiary alkanolamines, are stable in aqueous solution even in the presence of significant amounts of salts and in particular of sodium chloride. These solutions are stable independently on the presence of suitable stabilizers or solubilizers.

The compositions according to the invention can be produced using a simplified production process, which does not include the final purification steps of the whitening agent from the salts, such as osmotic purification.

The compositions according to the present invention comprise:

(a) one or more components selected from the group formed by:

mixtures of compounds of formula (I) $NR_1R_2R_3$ and compounds of formula (II)

formula (II)

wherein $R_1$, $R_2$ and $R_3$, each independently of the other, are selected in the group consisting of linear or branched $C_1$-$C_6$ alkyl groups, $C_3$-$C_6$ cycloalkyl groups, $C_1$-$C_6$ linear or branched hydroxyalkyl groups, $C_3$-$C_6$ hydroxycycloalkyl groups, $C_1$-$C_6$ linear or branched alkoxy groups; and wherein at least one of $R_1$, $R_2$ and $R_3$ is a $C_1$-$C_6$ linear or branched hydroxyalkyl group; $R_4$, $R_5$, $R_6$, $R_7$ each independently of the other, are selected in the group formed by H, $C_1$-$C_6$ linear or branched alkyl groups, $C_3$-$C_6$ cycloalkyl groups, $C_1$-$C_6$ linear or branched hydroxyalkyl groups, $C_3$-$C_6$ hydroxycycloalkyl groups; and X is selected in the group consisting of hydrogen, alkali metals, alkaline earth metals, ammonium and ammonium derived from the compound of formula (I), and compounds of formula (III)

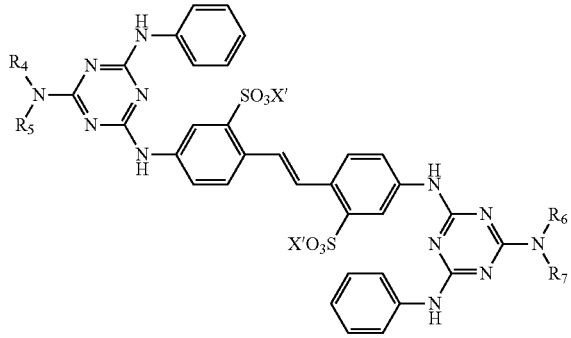

formula (III)

wherein $R_4$, $R_5$, $R_6$, $R_7$ are as above defined and X' is an ammonium ion derived from a compound of formula (I); and mixtures thereof
and
(b) compounds of formula (IV)

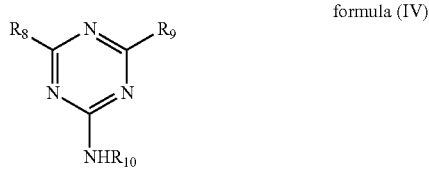

formula (IV)

wherein $R_8$ is selected in the group consisting of hydroxyl groups and halogen atoms;
$R_9$ is selected in the group consisting of hydroxyl and aniline groups;
$R_{10}$ is a phenyl group;
wherein the amount by weight of the compound of formula (IV) is between 0.1 ppm and 50 ppm with respect to the sum of the quantities by weight of the compounds of formula (I), (II) and (III).

The compositions according to the present invention may therefore include, in addition to a possible small amount of compound of formula (IV), alternatively:

a mixture of the compounds of formula (I) and of formula (II); or
compounds of formula (III); or
mixtures of compounds of formula (I), (II) and (III).

In other words, the compound of formula (IV), which is an impurity so far inevitably present in the stilbene optical whitening agents obtained by the processes of the prior art, in the composition according to the present invention it is present in a quantity between 0.1 ppm and 50 ppm (relative the sum of the whitening agents stilbene), preferably between 0.1 ppm and 40 ppm and more preferably between 0.1 ppm and 15 ppm.

Typically, the impurity that has to be kept in minimum amount in the compositions according to the present invention is 2-hydroxy-4,6-dianilino-1,3,5-triazine (AAHT), and the relative amounts by weight in the compositions according the invention is preferably comprised between 0.1 and 40 ppm, and more preferably between 0.1 ppm and 15 ppm with respect to the sum of the quantities by weight of the compounds of formula (I), (II) and (III).

As a further example of compounds of formula (IV) which may be present in the composition according to the present invention is to be mentioned 2-anilino-4,6-dihydroxy-1,3,5-triazine (AHHT). The composition according to the present invention may obviously contain mixtures of different compounds all represented by the general formula (IV).

As examples of groups $R_1$, $R_2$ and $R_3$ may be mentioned methyl, ethyl, propyl, isopropyl, n-butyl, isobutyl, sec-butyl, tert-butyl, n-pentyl, iso-pentyl, neopentyl, hexyl, cyclopentyl, cyclohexyl, hydroxyethyl, hydroxypropyl, hydroxybutyl.

As examples of groups $R_4$, $R_5$, $R_6$, $R_7$, $R_8$, $R_9$ may be mentioned methyl, ethyl, propyl, isopropyl, n-butyl, isobutyl, sec-butyl, tert-butyl, n-pentyl, iso-pentyl, neopentyl, hexyl, cyclopentyl, cyclohexyl, hydroxyethyl, hydroxypropyl, 2-hydroxypropyl, 3-hydroxypropyl, hydroxybutyl.

Preferably, the compound of formula (I) contained in the composition according to the present invention is an ethanolamine, in which $R_1$ and $R_2$ are selected from the group consisting of $C_1$-$C_3$ alkyl groups and $R_3$ is a group hydroxyethyl.

Even more preferably, the composition according to the preceding claim comprising a compound of formula (I) consisting of 2-(dimethylamino) ethanol.

The compounds of formula (II) contained in the composition according to the present invention are preferably chosen from the group formed by the following compounds of formula (IIa), (IIb), (IIc), (IId), (IIe), (IIf):

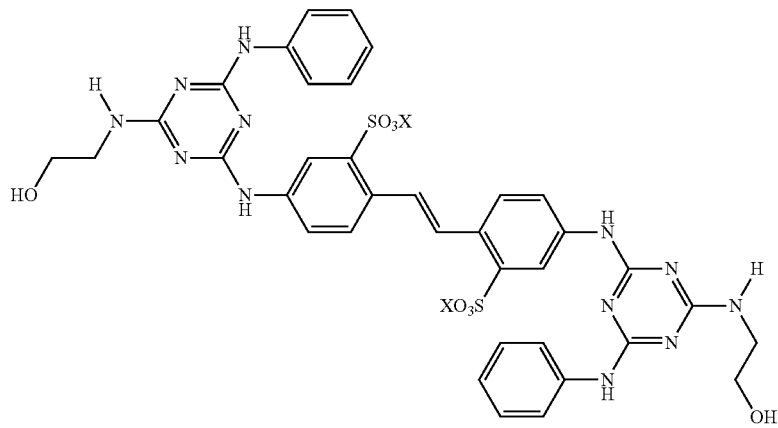

formula (IIa)

formula (IIb)
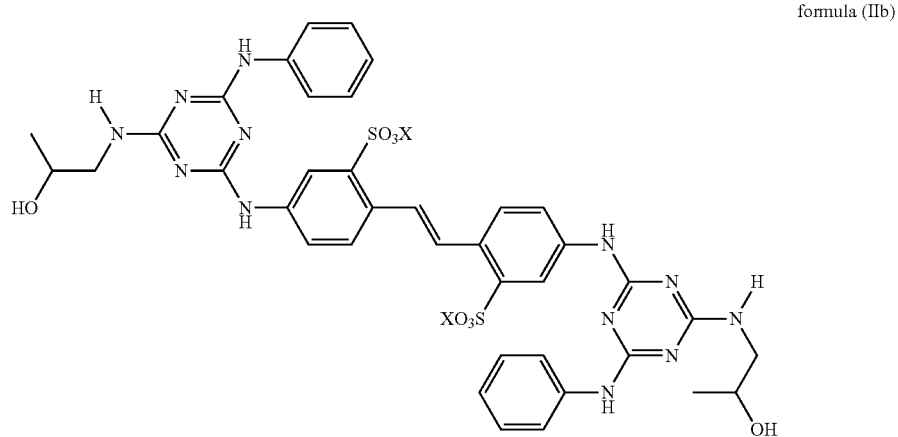
formula (IIc)
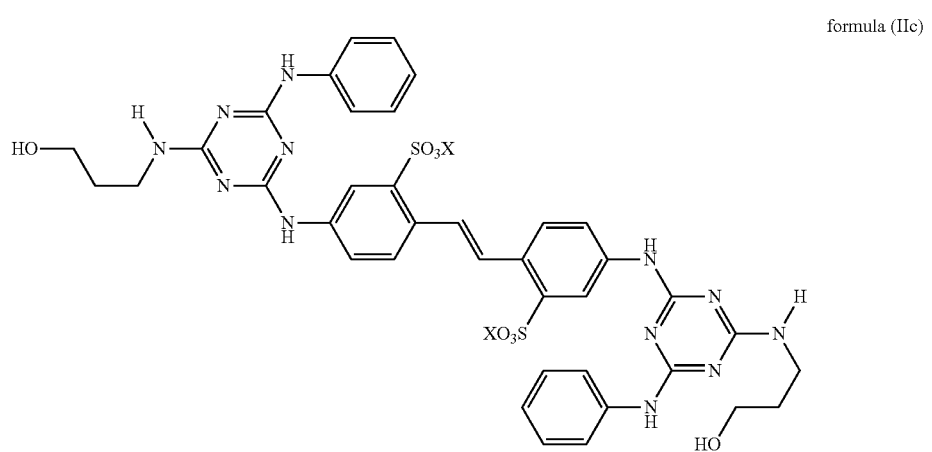
Formula (IId)
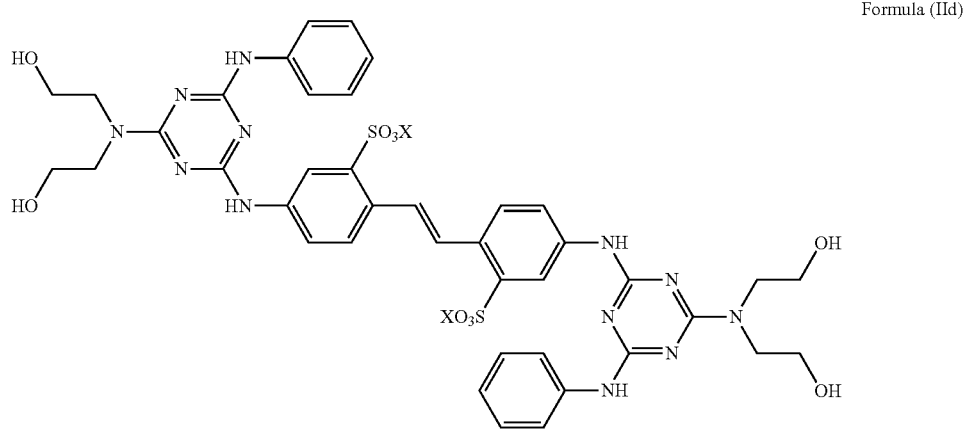

Formula (IIe)

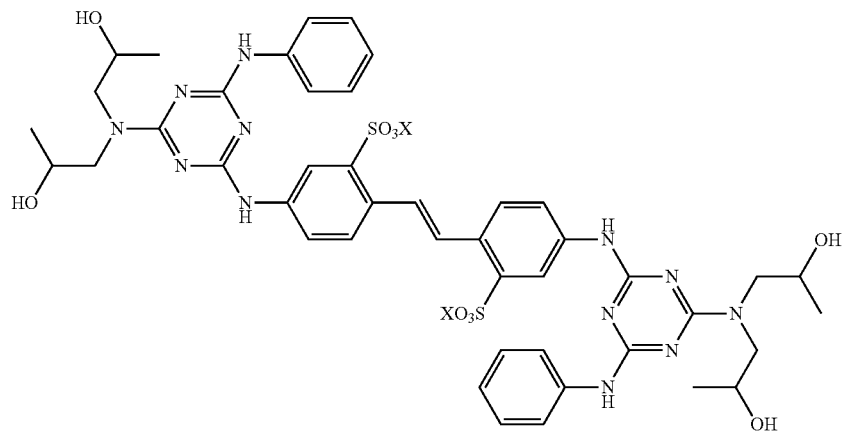

Formula (IIf)

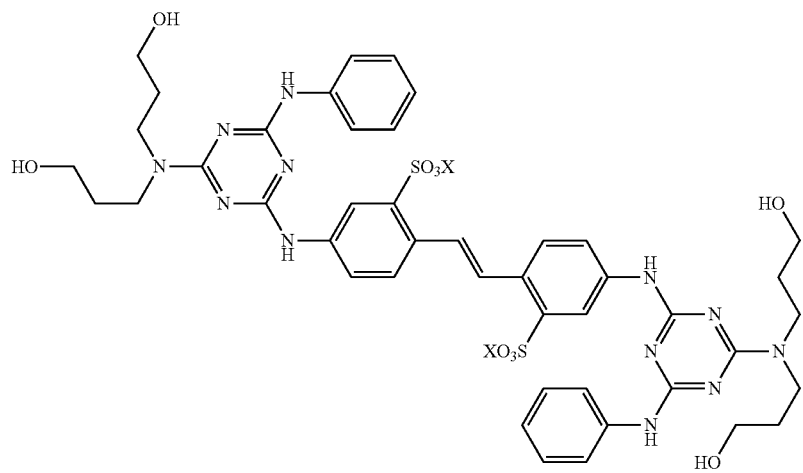

wherein X is as defined above.

The ratio between the amount in moles of the compound of formula (I) and of the compounds of formula (II) in the composition according to the invention is preferably less than 3. More preferably, this ratio is less than 2.5.

The compounds of formula (III), wherein X' is constituted by an ammonium ion derived from a compound of formula (I), are innovative fluorescent whitening agents deriving by salification between a whitening agent of formula (II) and an alkanolamine of formula (I). Such compounds of formula (III) exhibit particularly advantageous properties of stability in aqueous solution compared to those of the compounds known in the art.

Preferably, X' is an ammonium ion derived from a compound of formula (I), wherein $R_1$ and $R_2$ are selected from the group consisting of $C_1$-$C_3$ alkyl groups and $R_3$ is a hydroxyethyl group. Even more preferably, X' is an ammonium ion derived from 2-(dimethylamino)ethanol.

The composition according to the present invention therefore preferably includes compounds of formula (III) selected in the group consisting of the following formulas (IIIa), (IIIb), (IIIc), (IIId), (IIIe), (IIIf):

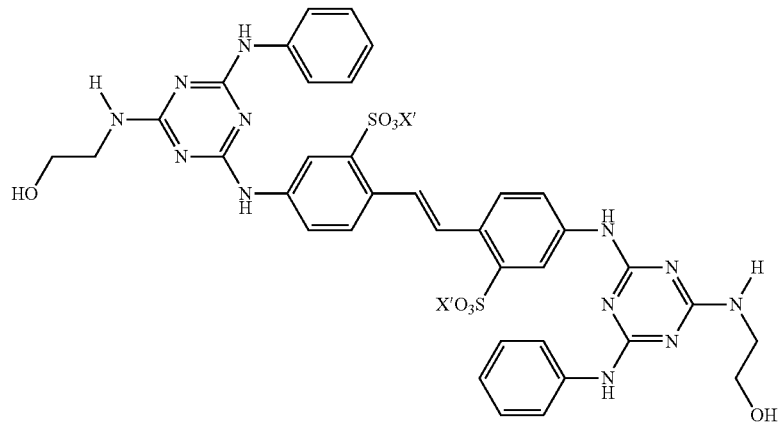
formula (IIIa)
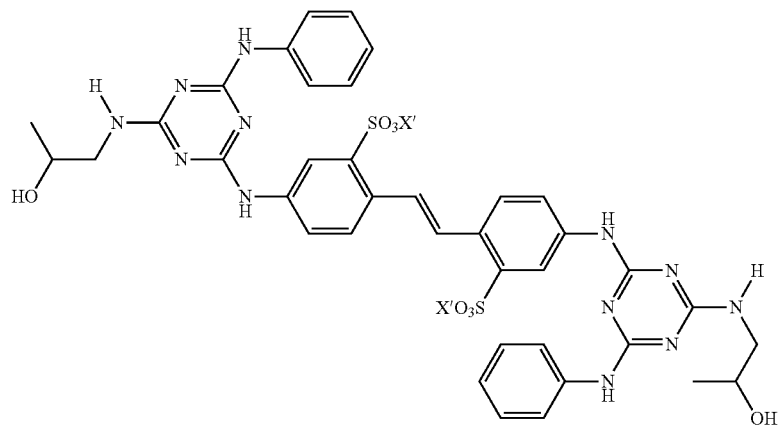
formula (IIIb)
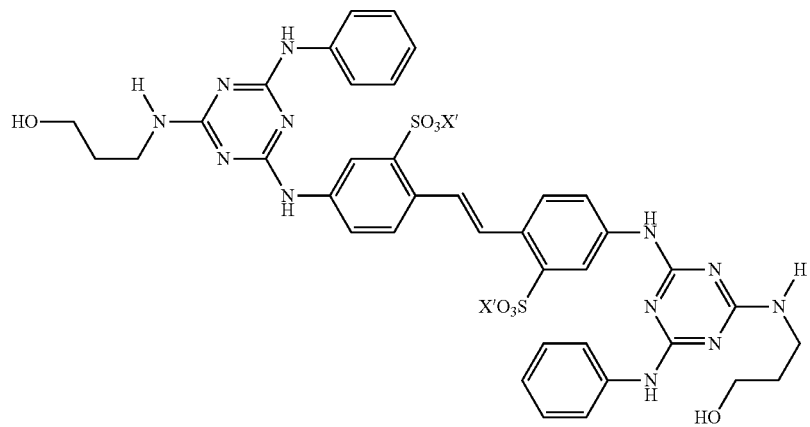
formula (IIIc)

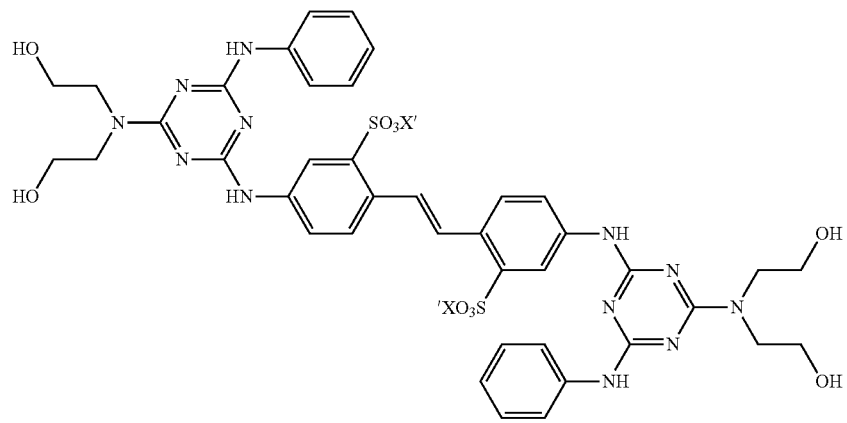
formula (IIId)
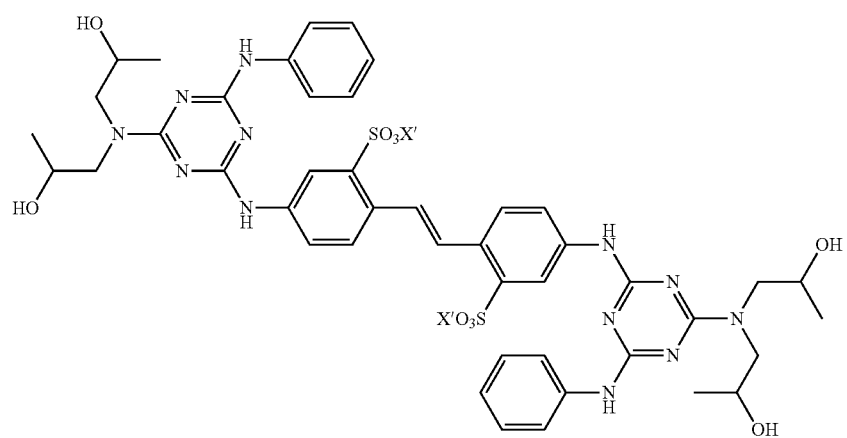
formula (IIIe)
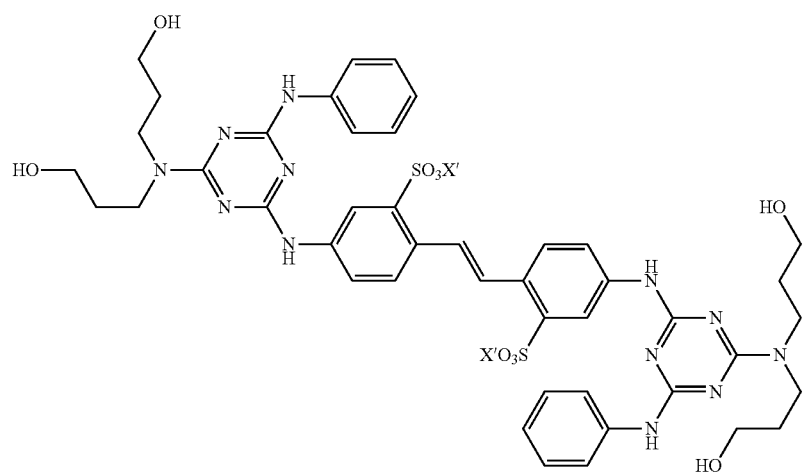
formula (IIIf)

wherein the group X' is an ammonium ion derived from 2-(dimethylamino) ethanol.

In a further aspect, the invention relates to a process for the preparation of a compound of formula (II) according to claim 1, or for the preparation of a compound of formula (III) according to claim 1.

The process can be conducted in a liquid system that consists of one or more solvents preferably selected among the polar solvents, such as ethers, ketones and mixtures thereof with water. Preferably, acetone, methyl ethyl ketone, acetone/water and methyl ethyl ketone/water can be used. Still more preferably there may be used mixtures of acetone and water wherein the acetone content varies between 20% and 70%.

In a first step of the process, cyanuric acid chloride is reacted with 4,4'-diaminostilbene-2,2'-disulphonic acid (DAS) in a suitable solvent medium. Said reaction is carried out at temperatures between −20° C. and +20° C., in the presence of bases, such as sodium bicarbonate or sodium hydroxide, so that the pH of the system is between 1 and 7. The ratio of moles of cyanuric chloride and 4,4'-diaminostilbene-2,2'-disulphonic acid (DAS) in this phase is about 2.00.

In a second phase of the process according to the present invention, which is generally carried out at temperatures between +10° C. and +60° C., the product obtained from said first step is reacted with aniline in the presence of bases such as sodium hydroxide, sodium bicarbonate or carbonate, so as to maintain the reaction mixture at a pH preferably between 4 and 8. Preferably, it is used in the second stage the suspension obtained in the first stage, without isolating the product.

According to a preferred embodiment of the invention, in said second step the reaction product of the first step of the process is reacted also with a small amount of amines of formula $NHR_4R_5$ and $NHR_6R_7$, wherein $R_4$, $R_5$, $R_6$, $R_7$ are defined as above. In this phase it is essential to maintain the ratio of moles of aniline and the moles of 4,4'-diaminostilbene-2,2'-disulphonic acid (DAS) used in said first step, to a value between 1.40 and 1.90, and preferably between 1.60 and 1.80. The ratio, in said second step of the procedure, between the moles of said amines $NHR_4R_5$ and $NHR_6R_7$ and the moles of 4,4'-diaminostilbene-2,2'-disulphonic acid (DAS) used in said first step is comprised between 0.10 and 0.60, preferably between 0.20 and 0.40.

In a third stage of the procedure the product obtained from said second step is reacted at a pH between 7 and 11, with amines $NHR_4R_5$ and $NHR_6R_7$, wherein $R_4$, $R_5$, $R_6$, $R_7$ are as defined above, and subsequent acidification. In said third step of the procedure, the ratio of moles of said amines $NHR_4R_5$ and $NHR_6R_7$ and the moles of 4,4'-diaminostilbene-2,2'-disulphonic acid (DAS) used in said first step is comprised between 1.60 and 2.60, and preferably from 2.00 to 2.30.

Furthermore, the condition must be satisfied that the ratio between: i) the sum of the moles of aniline and amines $NHR_4R_5$ and $NHR_6R_7$, used in said second and third phase, and ii) the moles of 4,4'-diaminostilbene-2,2'-disulphonic acid (DAS) used in said first step, is greater than or equal to 4.

Said third step preferably takes place at temperatures between 40° C. and 100° C. and in the presence of bases, such as sodium hydroxide, sodium carbonate or bicarbonate, in order to maintain the pH between 7 and 11. At the end of reaction the solvent is eliminated, for example by distillation, thereby obtaining an aqueous suspension of compound of formula (II), which separates. The liquid organic phase is separated from the aqueous phase, diluted with water at a temperature between 40° C. and 80° C. and acidified with an acid, for example hydrochloric, sulphuric or phosphoric acid.

An aqueous suspension is formed, generally containing a precipitate comprising a partially or completely acidified compound of formula (II).

For the preparation of a compound of formula (III), in a fourth phase of the process, the product obtained by said third step is reacted with a compound of formula (I) $NR_1R_2R_3$, wherein $R_1$, $R_2$ and $R_3$ are as above defined.

Said fourth step is conducted preferably at a temperature between 40° C. and 80° C.

As a matter of fact it was surprisingly discovered that, using the above molar ratios which establishes in the process according to the present invention a stoichiometric defect of moles of aniline and an excess of moles of amine $NHR_4R_5$ and $NHR_6R_7$, with respect to the moles of 4,4'-diaminostilbene-2,2'-disulphonic acid (DAS), and also a disproportion between the molar amounts of aniline and amine $NHR_4R_5$ and $NHR_6R_7$ in the second stage of the procedure, it is possible to drastically reduce or even eliminate the impurities formed of the compounds of formula (IV) in the process product. The product obtained with the process according to the present invention contains in fact between 0.1 and 40 pm and in some cases between 0.1 and 15 ppm of undesired compounds of formula (IV).

In this way, it is not necessary to perform treatments of purification of the obtained product, thanks to the fact that surprisingly the other possible impurities that can be formed in the process do not compromise the whitening properties and stability of the product obtained.

It has been observed, in fact, that significant amounts of fluorescent impurities different from the structures (II) and (III) can be formed in the production methods of optical brighteners according to the present invention, and in particular impurities of formula (V), which may then constitute a further component of the compositions according to the invention:

Formula (V)

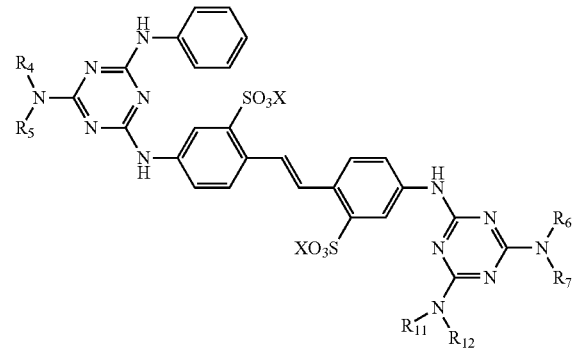

in which X, $R_4$, $R_5$, $R_6$ and $R_7$ are as defined for formula (II) and $R_{11}$, $R_{12}$, independently of one another, are selected from the group consisting of H, $C_1$-$C_6$ linear or branched alkyl groups, $C_3$-$C_6$ cycloalkyl groups, $C_1$-$C_6$ linear or branched hydroxyalkyl groups, $C_3$-$C_6$ hydroxycycloalkyl groups.

Typically, the amount of fluorescent impurities of formula (V) in the compositions according to the invention and in the products obtained by the process according to the invention may vary between 2 and 15% by weight, particularly between 5 and 10% by weight with respect to the total weight of the compounds of formula (I), (II) and (III).

Furthermore, it was observed that non-fluorescent triazine impurities of different nature with respect to those of formula (IV) can be formed, as for example 2,4,6-trianilino-1,3,5-triazine and, in the case of use of dialkanolamines, 2,4-dianilino-6-dialkanolamino-1,3,5-triazine; and 2-anilino-4,6-bis(dialkanolammino)-1,3,5-triazine. These impurities are generally present in a total amount of less than 2% by weight relative to the total weight of the compounds of formula (I), (II) and (III). In particular, it was observed that by operating according to the process of the present invention, the impurity 2,4,6-trianilino-1,3,5-triazine is always between 0.1 ppm and 25 ppm weight with respect to the total weight of the compounds of formula (I), (II) and (III). In the present description, fluorescent impurities is intended to indicate those impurities containing in the molecule one or more 4,4'-diamminostilbene-2,2'-disulfonic units, whereas non-fluorescent impurities indicate those impurities which do not contain 4,4'-diaminostilbene-2,2'-disulfonic units.

Suitable bases for the neutralization of the hydrochloric acid produced in the various process steps are hydroxides, carbonates or bicarbonates of alkali metals such as sodium, potassium or lithium. More preferably, sodium hydroxide, carbonate or bicarbonate may be used.

Suitable alkanolamines, to be used in the third stage of the process are preferably monoethanolamine, diethanolamine, monoisopropanolamine and diisopropanolamine. Even more preferably diethanolamine may be used.

As suitable neutralizing acid, hydrochloric acid may be advantageously used.

As suitable compound of formula (I), in the fourth step of the process, a dialkylethanolamine, even more preferably N,N-dimethylaminoethanol is preferably used.

In a further aspect, the invention relates to aqueous solutions of the compositions according to the present invention or of the product obtained according to the process of the invention, which preferably have active concentrations between 10-40% by weight, preferably 15-35% by weight and even more preferably 15-25% by weight.

Aqueous solutions according to the present invention may include additional components such as other whitening agents, inorganic salts, surfactants, preservatives, solubilizing agents or organic solvents.

Examples of optical brighteners used in the aqueous solution according to the present invention are tetra and/or hexasulphonated stilbene optical brighteners.

Examples of inorganic salts usable in the aqueous solution according to the present invention are sodium sulfate, ammonium chloride, potassium chloride and sodium chloride.

Examples of surfactants usable in the aqueous solution according to the present invention are sodium polynaphtalene sulphonates, ethoxylated fatty alcohols.

Examples of preservatives usable in the aqueous solution according to the present invention are glutaraldehyde, isothiazolinones, 2-bromo-2-nitropropane-1,3-diol.

Examples of solubilizing agents usable in the aqueous solution according to the present invention are polyethylene glycols, urea, caprolactam.

Examples of organic solvents usable in the aqueous solution according to the present invention are ethylene and propylene glycols.

The solutions according to the invention can be used for the whitening of natural fibers, semi-synthetic or synthetic or of paper, or in detergents.

In particular, the solutions according to the invention can be used for the whitening of paper and paperboard at any point in the process of production, either by adding said solutions directly in the dispersion of the fibers, or by adding them at the time of the subsequent surface treatments such as coating and the size press. The invention will be illustrated in the following with reference to the following non-limiting examples.

The concentrations of the solutions of optical brighteners are characterized by the parameter $E^{1\%}_{1cm}$ (or $E^1_1$), which corresponds to the value of specific extinction measured at the wavelength of maximum absorption of a solution containing 1% of the product in question, measured with a optical path of 1 cm.

In all examples, the extinction was measured with Perkin-Elmer Lamda UV-VIS spectrophotometer with an optical path of 1 cm.

The value of sodium chloride was determined by titrating by potentiometric chloride ions with Mettler automatic titrator with silver nitrate 0.1 M.

EXAMPLES

Example 1

Preparation of the Whitening Agent A

In 866 g of a 35% by weight mixture of acetone/water, 60.0 g of cyanuric chloride and 60.1 g of 4,4'-diaminostilbene-2,2'-disulphonic acid (DAS) were reacted for 4 hours, at a temperature between −10° C. and +15° C., in 2:1 molar ratio in the presence of 59 g of sodium bicarbonate, so as to maintain the pH between 4 and 6.

At the end of the reaction the obtained dispersion was reacted in 2 hours with 27.4 g of aniline in a molar ratio of 1.8, and 4.5 g of diethanolamine in a molar ratio of 0.2, at temperatures between 20 and 40° C. and by maintaining the pH between 6 and 8 by addition of 42.4 g of 30% aqueous soda.

At the end of the reaction the obtained dispersion was reacted with 39.0 g of diethanolamine, in a molar ratio of 2.28 with respect to the moles of DAS, by heating between 40° C. and 100° C. and by removing the acetone by distillation. In this phase the pH was maintained between 8 and 10 by addition of 46.8 g of 30% aqueous soda.

The hot organic phase was separated from the aqueous phase.

The organic phase was diluted with 500 g of demineralized water acidified with 30.6 g of concentrated hydrochloric acid and subsequently neutralized with 42.6 g of N,N-dimethylaminoethanol. The new organic phase was separated and diluted with 400 g of demineralized water that produced, after clarification by filtration, an aqueous 20% by weight solution of optical brightener.

The solution turned out to have an extinction value $E^1_1$ of 105, and NaCl content of about 0.58% by weight.

HPLC analysis with UV-VIS detector at 350 nm place the solution turned out to contain 15% of an optical brightening composition comprising the compounds of formulas (IId) and (IIId) in which $X=Na^+$ and $X'=(CH_3)_2NH^+(CH_2CH_2OH)$ (75% on a dry basis) and 1.4% of the compound of formula (V) wherein $R_4, R_5, R_6, R_7, R_{11}, R_{12}$ are hydroxyethyl group (7% on a dry basis) and by HPLC at 265 nm 3 ppm of 2-hydroxy-4,6-dianilino-1,3,5-triazine (AAHT) (15 ppm on a dry basis) (compound of formula IV wherein $R_8$ is the hydroxyl group, $R_9$ is the anilino group and $R_{10}$ is the phenyl group) with respect to the total content of compounds of formula (IId), (IIId) and (V).

Portions of this solution were subjected to stability tests at 5° C. The aqueous solution A was stable for three months at these temperatures.

The result is shown in Table 1.

Example 2

Preparation of the Whitening Agent B

In 866 g of a 35% by weight mixture of acetone/water, 60.0 g of cyanuric chloride and 60.1 g of 4,4'-diamminostilbene-2,2'-disulphonic acid (DAS) in 2:1 molar ratio were reacted for 4 hours, at a temperature between −10° C. and +15° C., in the presence of 59 g of sodium bicarbonate, to maintain the pH between 4 and 6.

At the end of the reaction the obtained dispersion was reacted in 2 hours with 30.2 g of aniline in a molar ratio of 2, at temperatures between 20 and 40° C. and by maintaining the pH between 6 and 8 by addition of 42.4 g of 30% aqueous soda.

At the end of the reaction the obtained dispersion was reacted with 39.0 g of diethanolamine, in a molar ratio of 2.28 with respect to the moles of DAS, by heating between 40 and 100° C. and by removing acetone by distillation. In this phase the pH was maintained between 8 and 10 by addition of 46.8 g of 30% aqueous soda.

The hot organic phase was separated from the aqueous phase.

The organic phase was diluted with 500 g of demineralized water acidified with 30.6 g of concentrated hydrochloric acid and subsequently neutralized with 42.6 g of N,N-dimethylaminoethanol. The new organic phase separated and was diluted with 400 g of demineralized water to produce an 20% by weight aqueous solution of optical brightener after clarification by filtration.

The solution turned out to have an extinction value $E^1_1$ equal to 105, and NaCl content equal to about 0.37% by weight.

HPLC analysis at 350 nm showed that the solution contained 17% of an optical brightening composition comprising the compounds of formulas (IId) and (IIId) in which $X=Na^+$ and $X'=(CH_3)_2NH^+(CH_2CH_2OH)$ (85% on a dry basis) and 0.8% of the compound of formula (V) wherein $R_4, R_5, R_6, R_7, R_{11}, R_{12}$ are hydroxyethyl group (4% on a dry basis) and HPLC analysis at 265 nm showed that the solution contained 16 ppm of 2-hydroxy-4,6-dianilino-1,3,5-triazine (AAHT) (80 ppm on a dry basis) (compound of formula (IV) wherein $R_8$ is the hydroxyl group, $R_9$ is the anilino group and $R_{10}$ is the phenyl group) with respect to the total content of compounds (IId), (IIId) and (V).

Portions of this solution were subjected to stability tests at 5° C. A solid separated from the solution after 40 days.

The result is shown in Table 1.

Example 3

Preparation of the Whitening Agent C

In 866 g of a 35% by weight mixture of acetone/water, 60.0 g of cyanuric chloride and 60.1 g of 4,4'-diamminostilbene-2,2'-disulphonic acid (DAS) in 2:1 molar ratio were reacted for 4 hours, at a temperature between −10° C. and +15° C., in the presence of 59 g of sodium bicarbonate, to maintain the pH between 4 and 6.

At the end of the reaction the obtained dispersion was reacted in 2 hours with 33.0 g of aniline in a molar ratio of 2.20, at temperatures between 20 and 40° C. and by maintaining the pH between 6 and 8 by addition of 42.4 g of 30% aqueous soda.

At the end of the reaction the obtained dispersion was reacted with 34.5 g of diethanolamine, in a molar ratio of 2.00 with respect to the moles of DAS, by heating between 40 and 100° C. and by removing acetone by distillation. In this phase the pH was maintained between 8 and 10 by addition of 46.8 g of 30% aqueous soda.

The hot organic phase was separated from the aqueous phase.

The organic phase was diluted with 500 g of demineralized water acidified with 30.6 g of concentrated hydrochloric acid and subsequently neutralized with 42.6 g of N,N-dimethylaminoethanol. The new organic phase separated and was diluted with 400 g of demineralized water to produce an 20% by weight aqueous solution of optical brightener after clarification by filtration.

The solution turned out to have an extinction value $E^1_1$ equal to 105, and NaCl content equal to about 0.22% by weight.

HPLC analysis at 350 nm showed that the solution contained 16.6% of an optical brightening composition comprising the compounds of formulas (IId) and (IIId) in which $X=Na^+$ and $X'=(CH_3)_2NH^+(CH_2CH_2OH)$ (83% on a dry basis) and 0.6% of the compound of formula (V) wherein $R_4, R_5, R_6, R_7, R_{11}, R_{12}$ are hydroxyethyl group (3% on a dry basis) and HPLC analysis at 265 nm showed that the solution contained 24 ppm of 2-hydroxy-4,6-dianilino-1,3,5-triazine (AAHT) (120 ppm on a dry basis) (compound of formula (IV) wherein $R_8$ is the hydroxyl group, $R_9$ is the anilino group and $R_{10}$ is the phenyl group) with respect to the total content of compounds (IId), (IIId) and (V).

Portions of this solution were subjected to stability tests at 5° C. A solid separated from the solution after 35 days.

The result is shown in Table 1.

TABLE 1

|   | 1° step | | 2° step | | 3rd step | Stability | | | | Composition | | |
| --- | --- | --- | --- | --- | --- | --- | --- | --- | --- | --- | --- | --- |
|   | cyanuric chloride moles | DAS moles | Aniline moles | Diethanol amine moles | Diethanol amine moles | 5° C. | E11 | NaCl % | Dry % | compound of formula (IId) % | compound of formula (V) % | AAHT (form. IV) ppm |
| A | 2.00 | 1.00 | 1.80 | 0.20 | 2.28 | stable for 3 months | 105 | 0.58 | 20 | 75 | 7 | 15 |
| B | 2.00 | 1.00 | 2.00 | 0.00 | 2.28 | separation after 40 days | 105 | 0.37 | 20 | 85 | 4 | 80 |
| C | 2.00 | 1.00 | 2.20 | 0.00 | 2.00 | separation after 35 days | 105 | 0.22 | 20 | 83 | 3 | 120 |

Application Example 1

The whitening agent A obtained as described in Example 1 was evaluated in its application by coating, i.e. a surface treatment which involves the application on the sheet surface of one or more uniform layers of compositions that are essentially formed of a mineral pigment and an adhesive (binder).

In the application examples, the coated specimens were obtained by applying, by means of a doctor blade for laboratory use, a uniform layer of a coating prepared according to the following recipe: (standard coating)

80 parts of Hydrocarb 90AV calcium carbonate
20 parts of Hydrafine kaolin
12 parts of Stironal D517 synthetic binder
0.5 parts of Finnfix 10 carboxymethylcellulose
Sodium hydroxide solution (10% NaOH) to pH~9
Demineralized water up to final dry of 65%.

The used supporting paper was the type "Fabriano 2 smooth" basis weight 110 g/m².

At the end of the application the specimens were dried at room temperature for one hour.

The degree of whiteness was detected by means of an Elrepho LWE450-X Datacolor reflectometer.

The thus prepared standard coating was applied as such on paper substrate to produce a reference degree of whiteness (dosage optical brightener=0).

Subsequently the standard coating was additioned with 1.40% by weight of the whitening agent A formulated to $E^1_1=105$, then applied on the support; the applicative yield of the whitening agents can be quantified through the increase of the degree of whiteness of paper after application in comparison with the reference degree of white.

The obtained values are shown in Table 2

TABLE 2

| | FWA dosage | D65/10° Brightness | D65/10° CIE Whiteness |
|---|---|---|---|
| reference degree of whiteness | 0.0% | 88.1 | 80.07 |
| whitening agent A | 1.4% | 96.5 | 101.61 |

The invention claimed is:

1. A composition comprising:
   (a) one or more components selected in the group consisting of:
   mixtures of compounds having formula (I) $NR_1R_2R_3$ and compounds having formula (II)

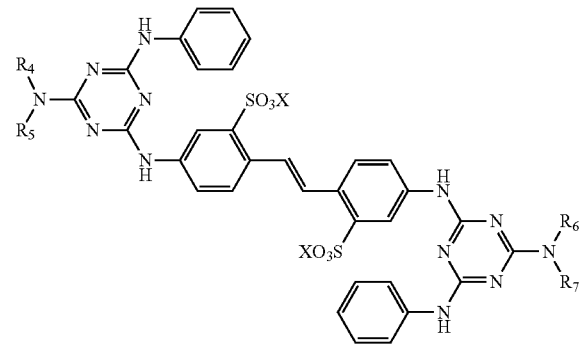

formula (II)

wherein $R_1$, $R_2$ and $R_3$, independently of each other, are selected in the group consisting of $C_1$-$C_6$ linear or branched alkyl groups, $C_3$-$C_6$ cycloalkyl groups, $C_1$-$C_6$ linear or branched hydroxyalkyl groups, $C_3$-$C_6$ hydroxycycloalkyl groups, $C_1$-$C_6$ linear or branched alkoxyl groups; and wherein at least one among $R_1$, $R_2$ and $R_3$ is a $C_1$-$C_6$ linear or branched hydroxyalkyl group; $R_4$, $R_5$, $R_6$, $R_7$, independently of each other, are selected in the group consisting of H, $C_1$-$C_6$ linear or branched alkyl groups, $C_3$-$C_6$ cycloalkyl groups, $C_1$-$C_6$ linear or branched hydroxyalkyl groups, $C_3$-$C_6$ hydroxycycloalkyl groups; and X is selected in the group consisting of hydrogen, alkaline metals, alkaline-earth metals, ammonium or ammonium derived from a compound of formula (I);

compounds of formula (III)

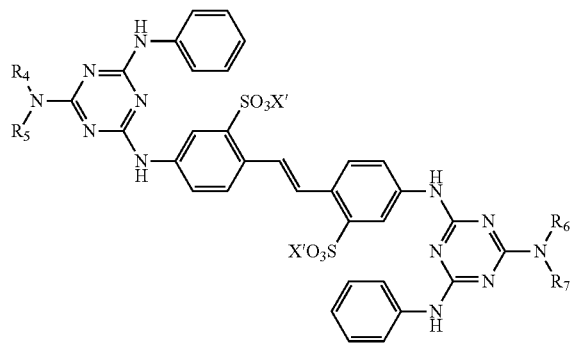

formula (III)

wherein $R_4$, $R_5$, $R_6$, $R_7$, are as above defined and X' is an ammonium derivative of a compound of formula (I); and mixtures thereof; and (b) one or more components selected among the compounds of formula (IV)

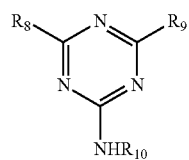

formula (IV)

wherein $R_8$ is selected in the group consisting of hydroxyl groups and halogen atoms;
$R_9$ is selected in the group consisting of hydroxyl groups and aniline groups;
$R_{10}$ is a phenyl group;
wherein the weight quantity of the compound of formula (IV) is between 0.1 ppm and 50 ppm with respect to the sum of the weights of the compounds of formula (I), (II) and (III).

2. A composition according to claim 1, wherein said compounds of formula (IV) are selected in the group consisting of 2-hydroxy-4,6-dianilino-1,3,5-triazine and 2-anilino-4,6-dihydroxy-1,3,5-triazine and mixtures thereof.

3. A composition according to claim 2, wherein the weight quantity of said compounds of formula (IV) is between 0.1 ppm and 15 ppm with respect to the sum of the weights of the compounds of formula (I), (II) and (III).

4. A composition according to claim 1, wherein it also comprises one or more compounds of formula (V)

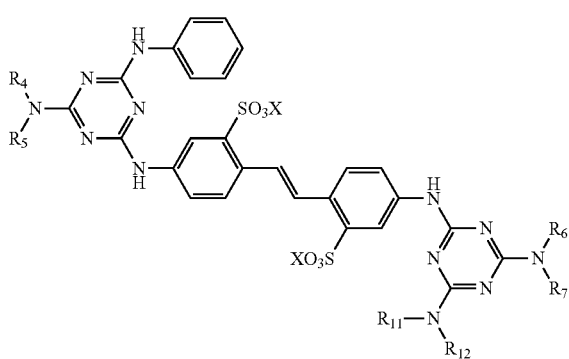

Formula (V)

wherein X, $R_4$, $R_5$, $R_6$ and $R_7$ are the same as defined in claim 1 and $R_{11}$, $R_{12}$, independently of each other, are selected in the group consisting of H, $C_1$-$C_6$ linear or branched alkyl groups, $C_3$-$C_6$ cycloalkyl groups, $C_1$-$C_6$ linear or branched hydroxyalkyl groups, $C_3$-$C_6$ hydroxycycloalkyl groups; wherein the weight quantity of said compound of formula (V) is between 2% and 15% with respect to the total weight of the compounds of formula (I), (II) and (III).

5. A composition according to claim 4, wherein the weight quantity of said compound of formula (V) is between 5% and 10% with respect to the total weight of the compounds of formula (I), (II) and (III).

6. A composition according to claim 1, wherein in said compounds of formula (I), $R_1$ and $R_2$ are selected in the group consisting of $C_1$-$C_3$ alkyl groups and $R_3$ is a hydroxyethyl group.

7. A composition according to claim 6, wherein said compound of formula (I) is 2-(dimethylamino)ethanol.

8. A composition according claim 7, wherein said compound of formula (II) is selected in the group consisting of the following compounds of formula (IIa), (IIb), (IIc), (IId), (IIe), (IIf):

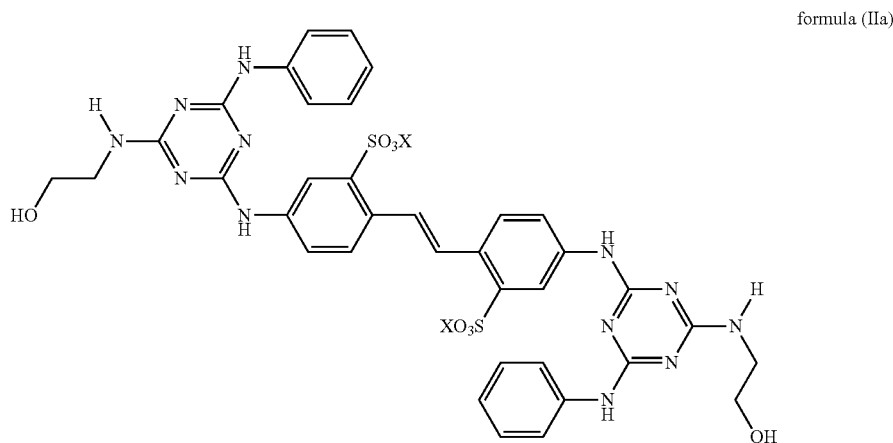

formula (IIa)

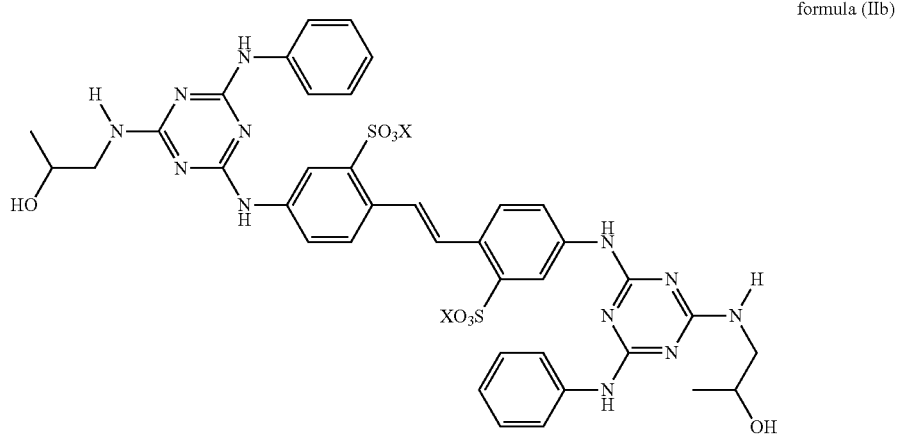

formula (IIb)

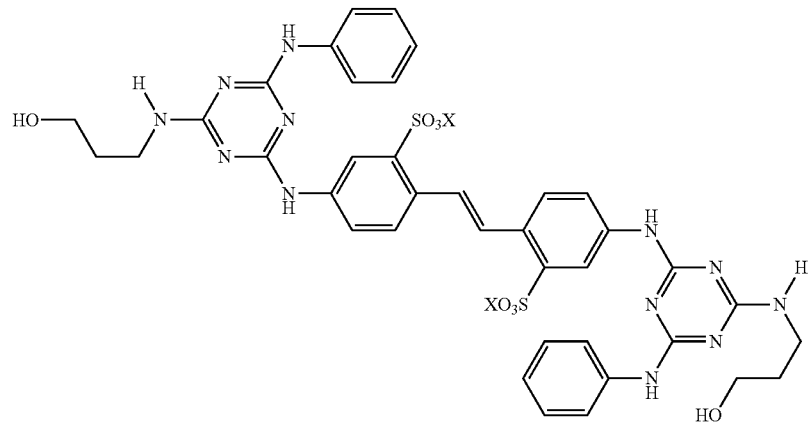
formula (IIc)
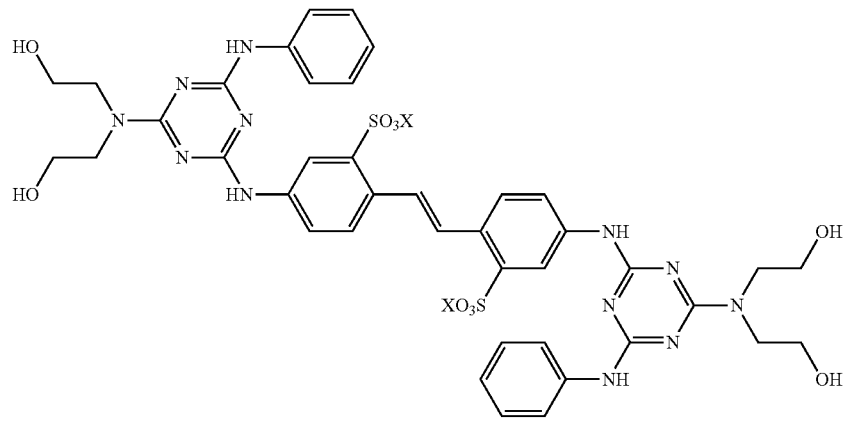
formula (IId)
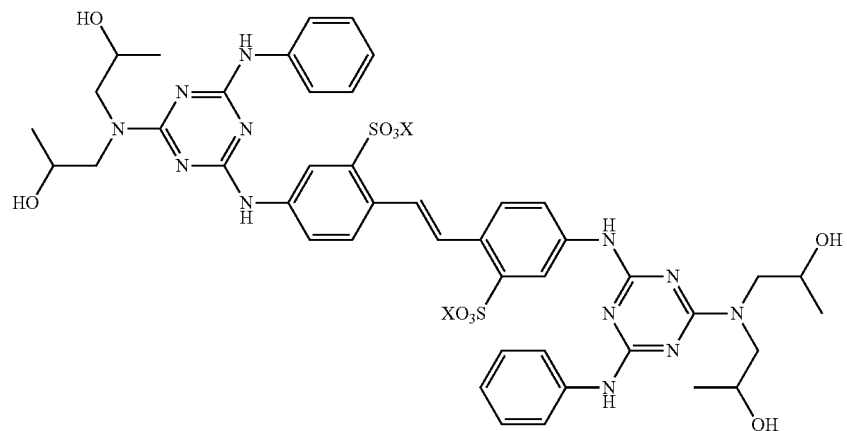
formula (IIe)

formula (IIf)
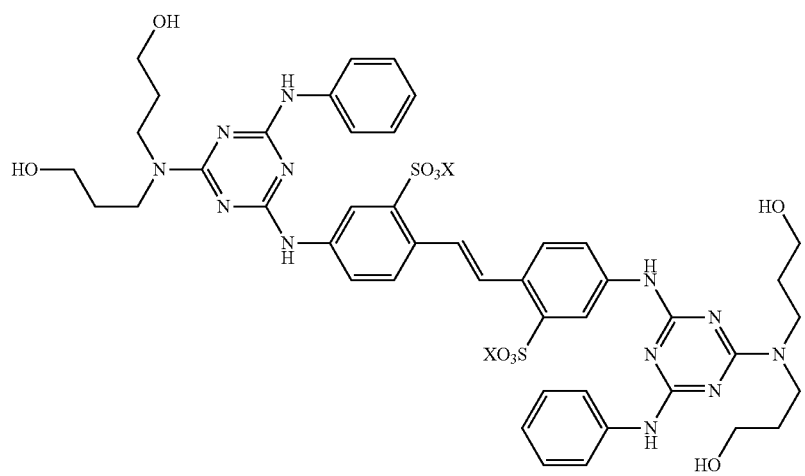
wherein X is as defined above.
9. A composition according to claim 7, wherein said compound of formula (III) is selected in the group consisting of the compounds having following formulas (IIIa), (IIIb), (IIIc), (IIId), (IIIe), (IIIf):
formula (IIIa)
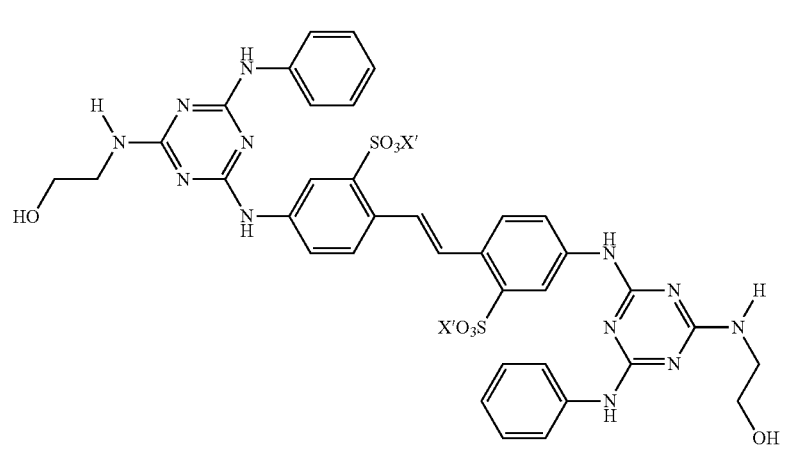
formula (IIIb)
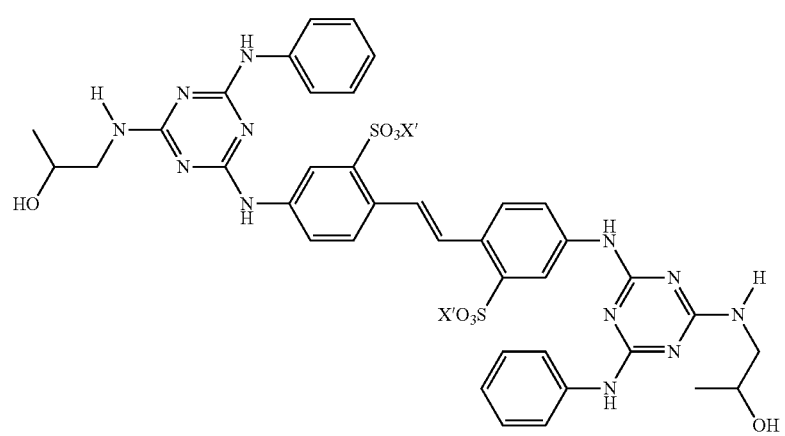

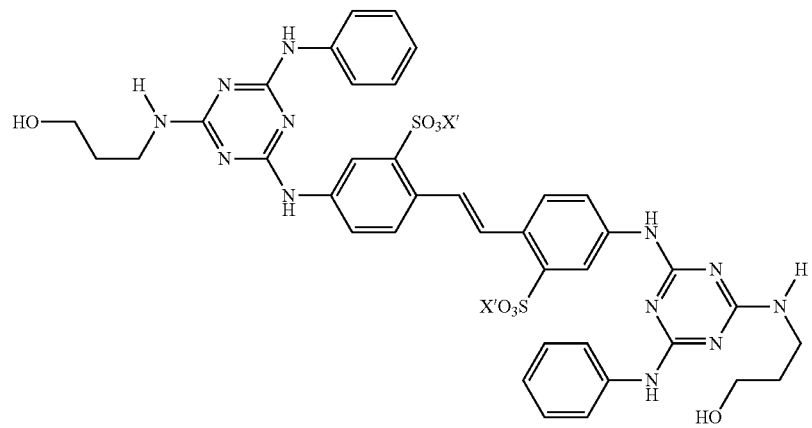
formula (IIIc)
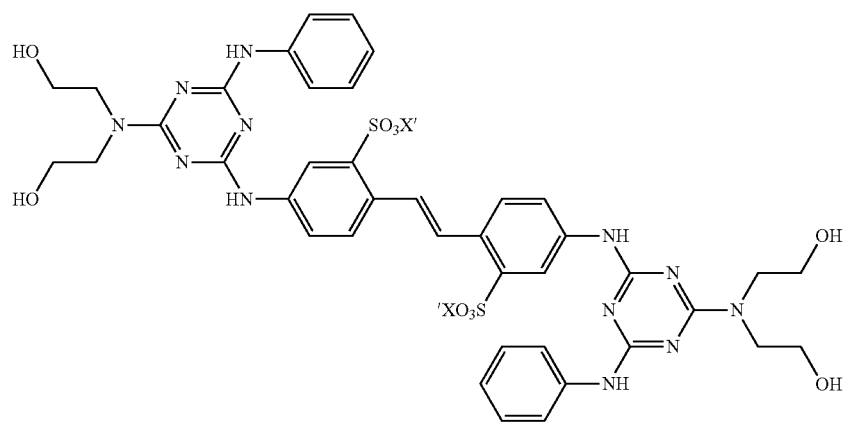
formula (IIId)

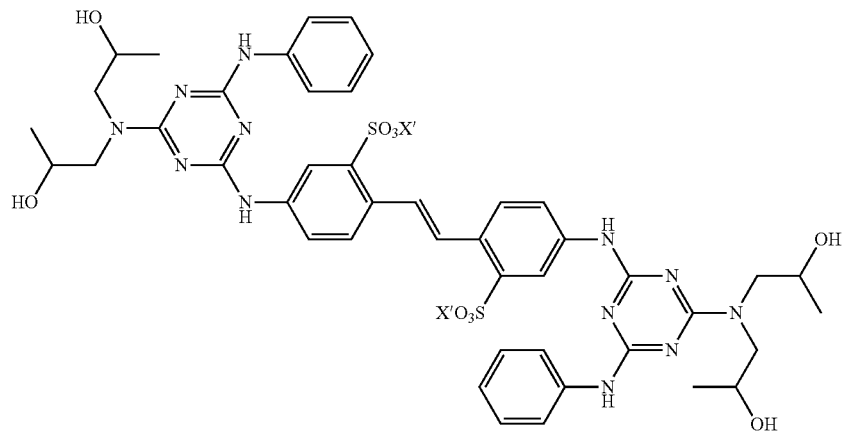

formula (IIIe)

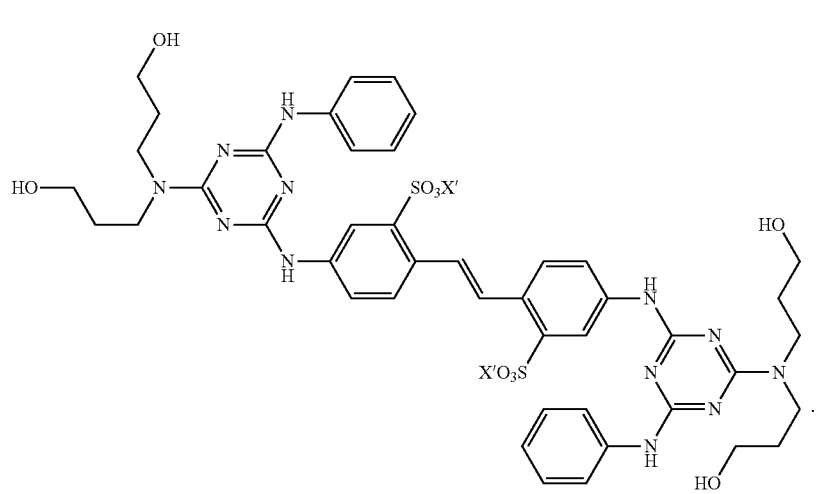

formula (IIIf)

10. A process for the preparation of a composition according to claim 1, comprising:
- a first step of reacting cyanuric chloride with 4,4'-diaminostilbene-2,2'-disulfonic acid (DAS);
- a second step of reacting the product obtained from said first step with aniline, wherein the ratio, between the moles of aniline and the moles of 4,4'-diaminostilbene-2,2'-disulfonic acid (DAS) used in said first step, is between 1.40 and 1.90;
- a third step of reacting the product obtained from said second step with $NHR_4R_5$ and $NHR_6R_7$ amines, wherein $R_4$, $R_5$, $R_6$, $R_7$ are as defined in claim 1, wherein the ratio between the moles of said $NHR_4R_5$ and $NHR_6R_7$ amines and the moles of 4,4'-diaminostilbene-2,2'-disulfonic acid (DAS) used in said first step is between 1.60 and 2.60;
- with the proviso that the ratio between the sum of the moles of aniline and of amines used in said second and third step, and the moles of 4,4'-diaminostilbene-2,2'-disulfonic acid (DAS) used in said first step is equal or greater than 4.

11. A process according to claim 10, wherein in said second step the product obtained from said first step is reacted with aniline and with $NHR_4R_5$ and $NHR_6R_7$ amines, wherein $R_4$, $R_5$, $R_6$, $R_7$ are as defined above, wherein the ratio, between the moles of said $NHR_4R_5$ and $NHR_6R_7$ amines and the moles of 4,4'-diaminostilbene-2,2'-disulfonic acid (DAS) used in said first step, is between 0.10 and 0.60.

12. A process according to the preceding claim 11, wherein:
- in said second step, the ratio between the moles of aniline and the moles of 4,4'-diaminostilbene-2,2'-disulfonic acid (DAS) used in said first step, is between 1.60 and 1.80; and the ratio between the moles of said $NHR_4R_5$ and $NHR_6R_7$ amines and the moles of 4,4'-diaminostilbene-2,2'-disulfonic acid (DAS) used in said first step, is between 0.20 and 0.40; and
- in said third step, the ratio between the moles of said $NHR_4R_5$ and $NHR_6R_7$ amines and the moles of 4,4'-diaminostilbene-2,2'-disulfonic acid (DAS) used in said first step, is between 2.00 and 2.30.

13. A process according to claim 10, comprising a fourth step of reacting a product obtained from said third step with a compound of formula (I) $NR_1R_2R_3$, wherein $R_1$, $R_2$ and $R_3$ are as defined above.

14. A process according to claim 10, wherein both said $NHR_4R_5$ and $NHR_6R_7$ amines are diethanolamine.

15. A process according to claim 13, wherein said compound of formula (I) is N,N-dimethylaminoethanol.

16. A product obtained by means of the process according to claim 10.

17. A water solution comprising a composition according to claim 1.

18. A method for the whitening treatment of paper, or the whitening treatment of natural, semi-synthetic or synthetic fibers comprising contacting paper, natural, semi-synthetic or synthetic fibers with a water solution according to claim 17.

19. A detergent comprising a water solution of claim 17.

* * * * *